US006475481B2

(12) United States Patent
Talmadge

(10) Patent No.: US 6,475,481 B2
(45) Date of Patent: *Nov. 5, 2002

(54) PURGING OF STEM CELL PRODUCTS

(75) Inventor: James E. Talmadge, Bellevue, NE (US)

(73) Assignee: Canji, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/193,599

(22) Filed: Nov. 17, 1998

(65) Prior Publication Data

US 2002/0081281 A1 Jun. 27, 2002

Related U.S. Application Data

(60) Provisional application No. 60/065,638, filed on Nov. 18, 1997.

(51) Int. Cl.[7] .................. A01N 63/00; A61K 48/00; C12P 21/06; C12N 5/00
(52) U.S. Cl. .................. 424/93.3; 424/93.21; 424/93.6; 435/325; 435/69.1
(58) Field of Search .................. 424/93.21, 93.6; 435/320.1, 325, 69.1, 235.1; 514/44; 536/23.1

(56) References Cited

U.S. PATENT DOCUMENTS 5,932,210 A * 8/1999 Gregory et al. ............ 424/93.2

FOREIGN PATENT DOCUMENTS

WO  WO 96/25507  * 8/1996

OTHER PUBLICATIONS

Kvalheim et al., "Purging of tumor cells from leukopheresis products: experimental and clinical aspects", J. Hematother., 5:427–436, Aug. 1996.*
Clarke et al., "A recombinant bcl–xs adenovirus selectively induces apoptosis in cancer cells but not in normal bone marrow cells", Proc. Natl. Acad. Sci. USA, 92:11024–11028, Nov. 1995.*
Seth et al., "Adenovirus–mediated gene transfer to human breast tumor cells: an approach for cancer gene therapy and bone marrow purging", Cancer Res., 56:1346–1351, Mar. 1996.*
Wroblewski et al., "Selective elimination (purging) of contaminating malignant cells from hematopoietic stem cell autografts using recombinant adenovirus", Cancer Gene Ther., 3(4):257–264, Jul. 1996.*
Chen et al., "Selective transgene expression for detection and elimination of contaminating carcinoma cells in hematopoietic stem cell sources", J. Clin. Invest., 98(11):2539–2548, Dec. 1996.*
Kim et al., "A novel gene therapy strategy for elimination of prostate carcinoma cells from human bone marrow", Hum. Gene Ther., 8:157–170, Jan. 1997.*
Reisner et al., "Hematopoietic stem cell transplantation for cancer therapy", Curr. Opin. Immunol., 7:687–693, Oct. 1995.*

* cited by examiner

Primary Examiner—Deborah J. Reynolds
Assistant Examiner—Joseph Woitach
(74) Attorney, Agent, or Firm—Townsend and Townsend and Crew LLP

(57) ABSTRACT

Methods for purging stem cell products of tumor cells and for treating an individual having a disease which is treated by myeloablative therapy and stem cell rescue using a purged product are provided.

52 Claims, 12 Drawing Sheets

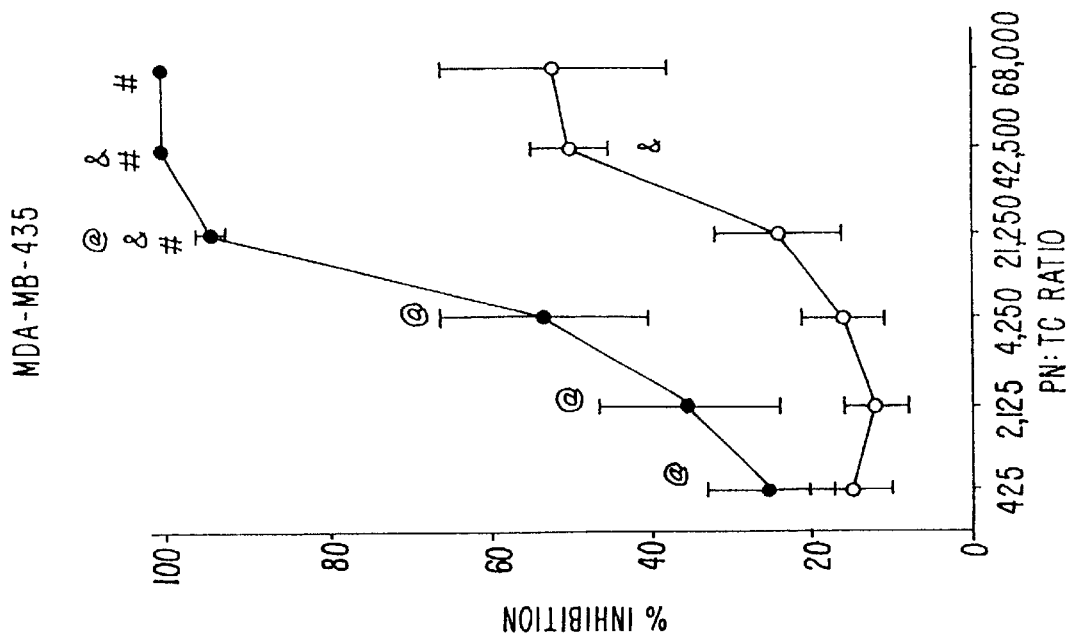
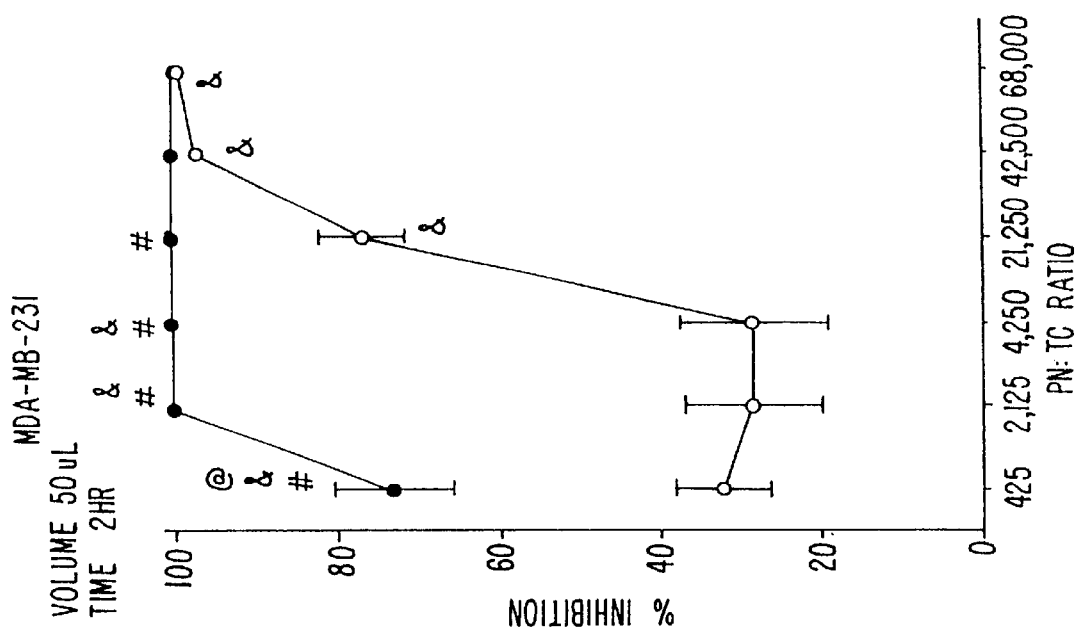
FIG. 2A1.
FIG. 2A2.

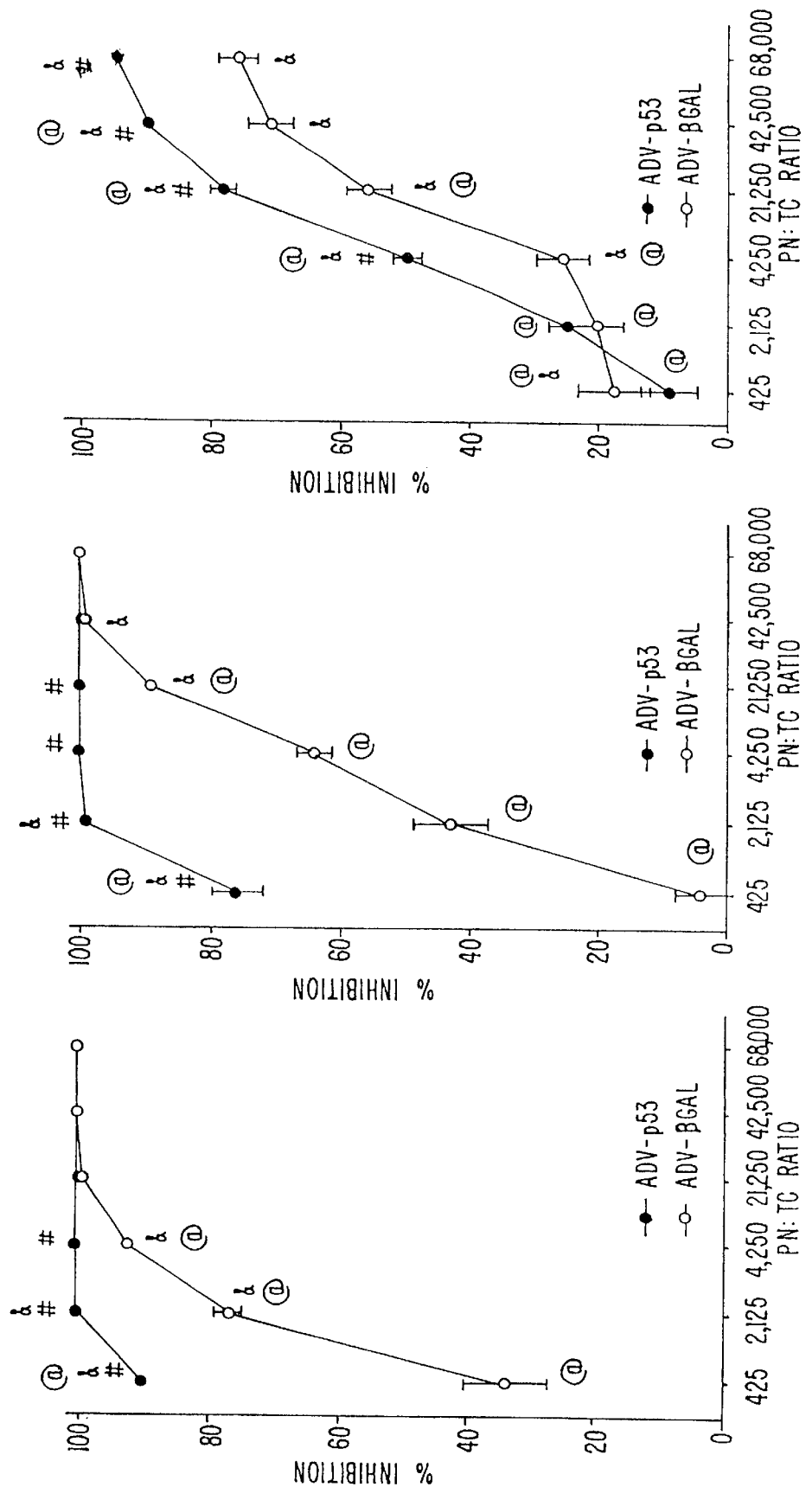

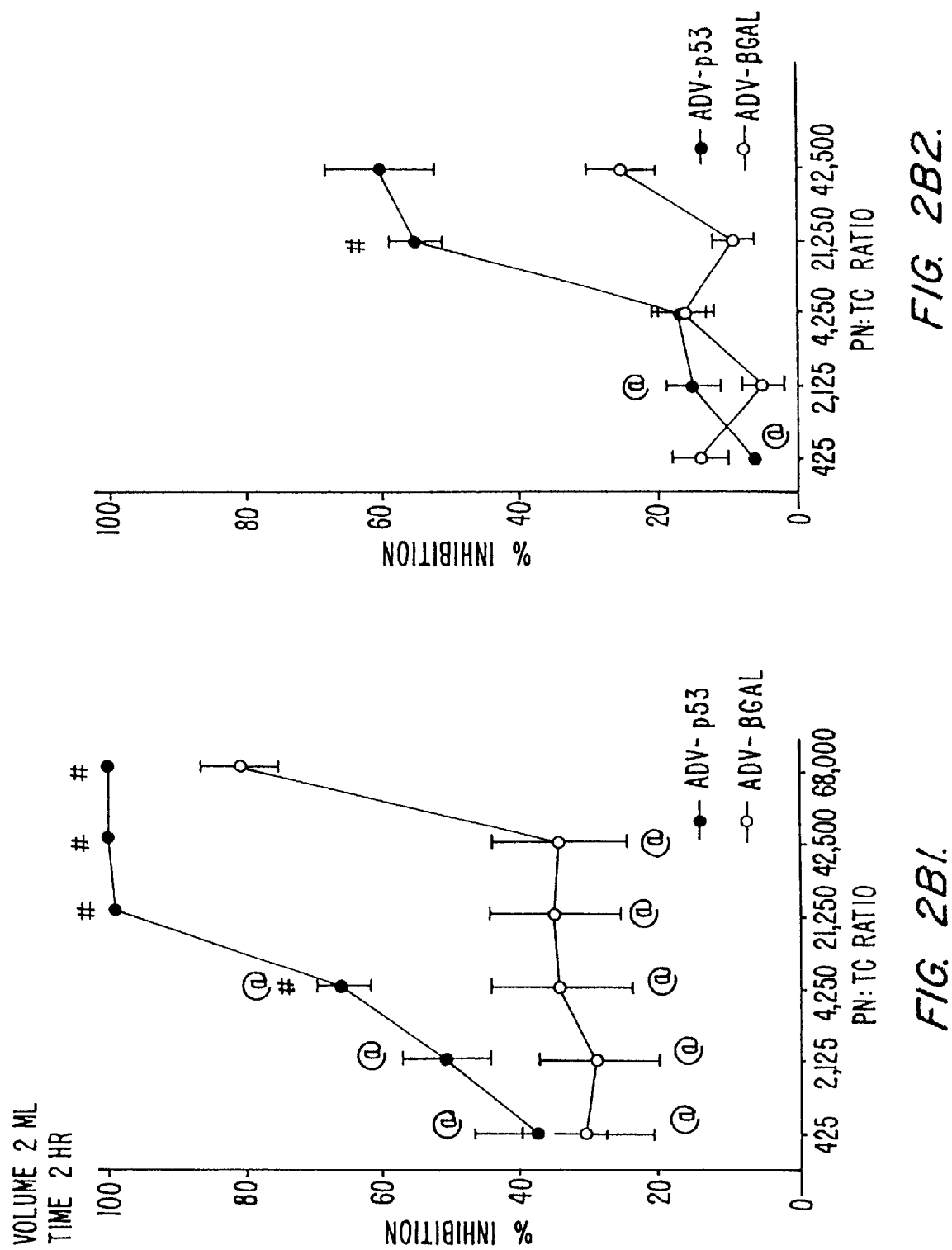
FIG. 2B1.
FIG. 2B2.

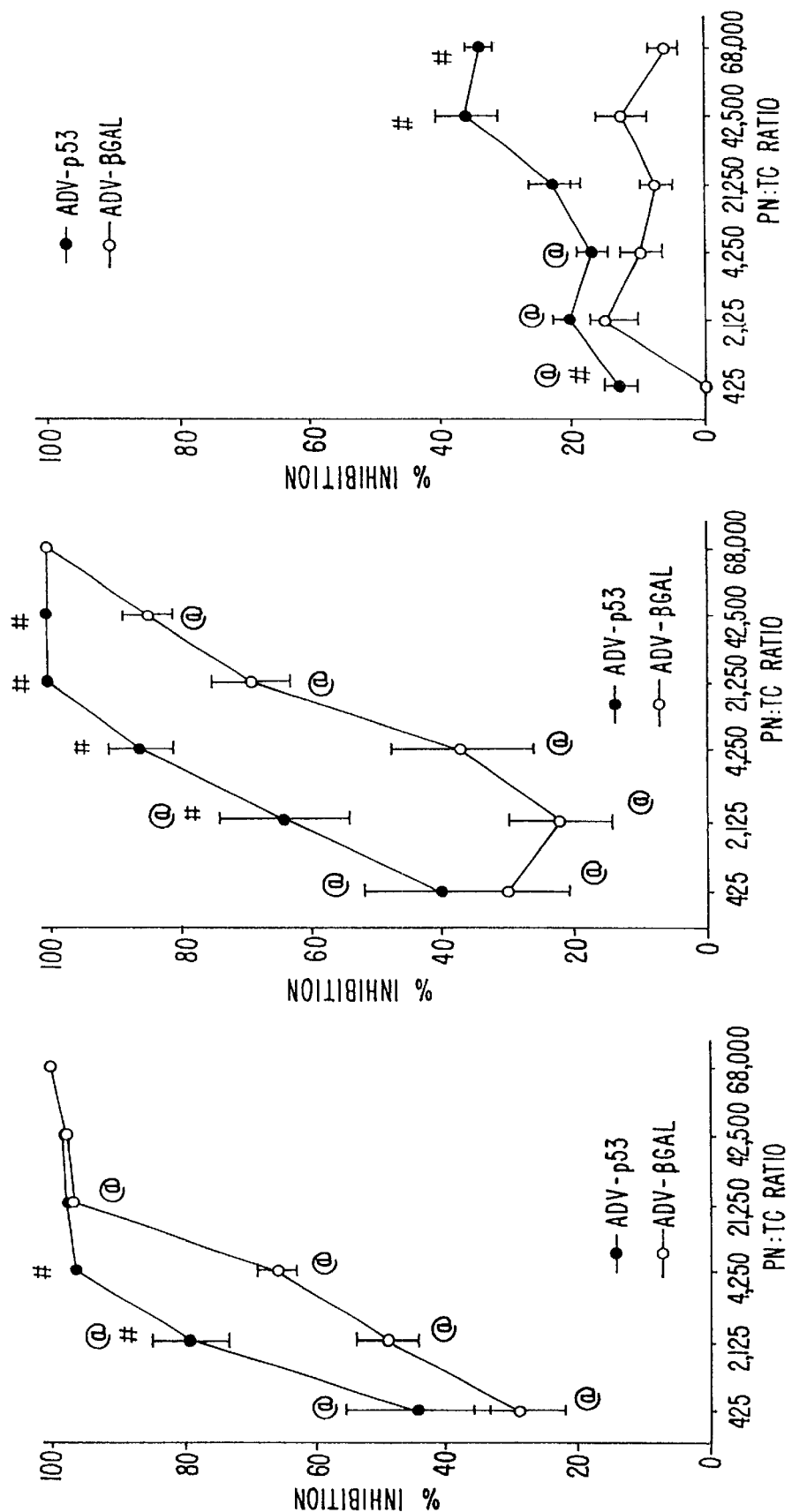

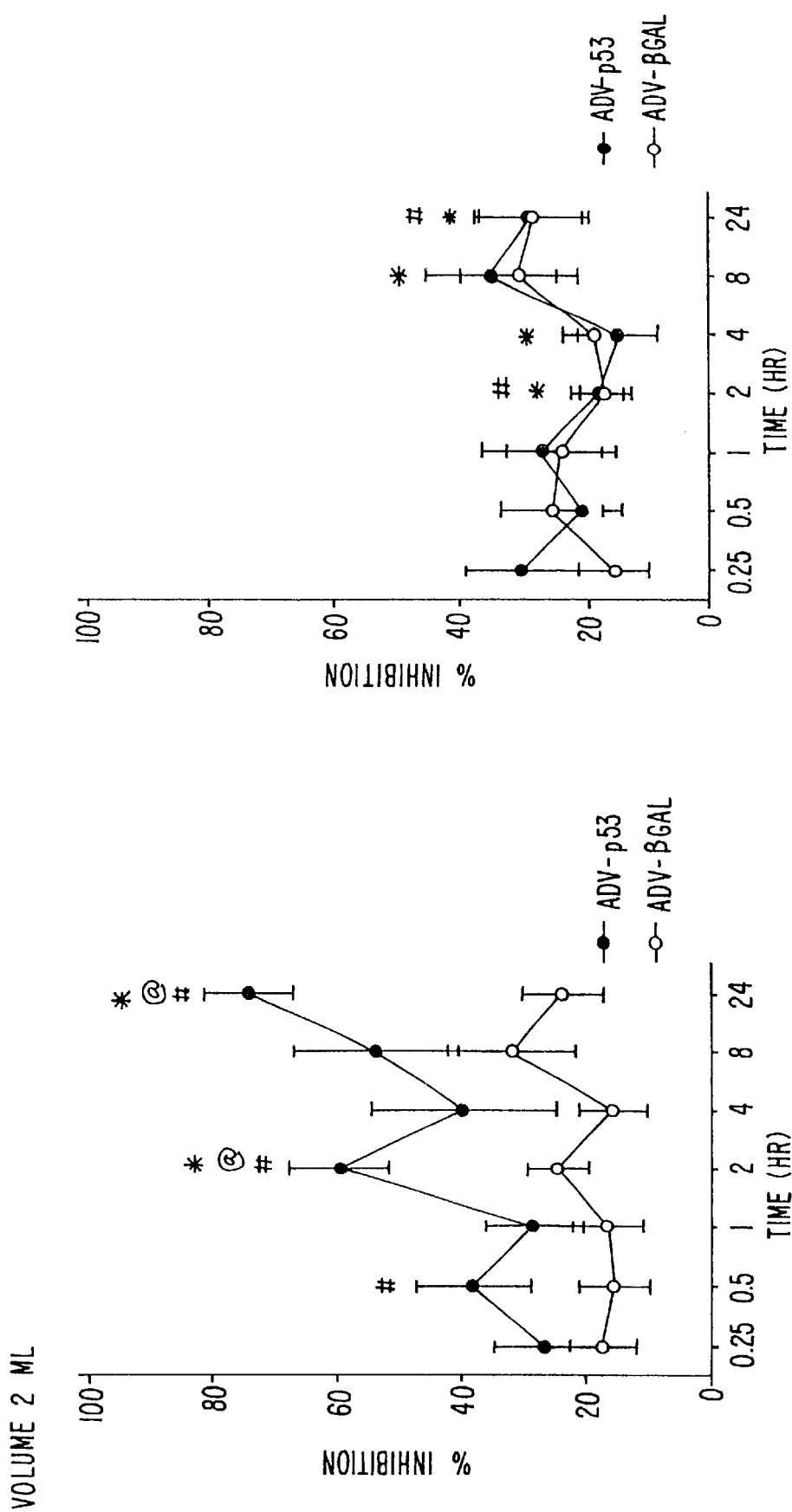

PURGING OF STEM CELL PRODUCTS

This Application claims benefit to provisional application Ser. No. 60/065,638, filed Nov. 18, 1997.

BACKGROUND OF THE INVENTION

Treatment of cancer patients with chemotherapeutic agents remains the primary method of treating systemic disease. There is a direct association between chemotherapeutic dose intensity and clinical response rate. However, increasing doses of chemotherapy have significant side effects including the widespread destruction of bone marrow hematopoietic precursor cells with concomitant destruction of peripheral myeloid and lymphoid cellularity. Thus, stem cell transplantation is used in conjunction with high dose chemotherapy, frequently in combination with growth factor support, to facilitate the recovery of the hematopoietic system following chemotherapy.

There are two general types of stem cell transplantation: allogeneic and autologous. In allogeneic transplantation, stem cells from a donor other than the patient are infused. This protocol carries a high mortality rate due primarily to graft-versus-host disease wherein the transplanted cells attack the patient's own tissues. Autologous stem cell transplantation (or "stem cell rescue") is a protocol wherein the patient's stem cells are isolated prior to the high dose chemotherapy and subsequently reinfused. Because autologous transplantation does not result in graft-versus-host disease, the procedure related mortality is reduced compared to allogeneic transplantation. However, in a disease and stage dependent manner, autologous transplantation may result in the reinfusion of tumor cells from within the stem cell product.

Treatment with high-dose chemotherapy in conjunction with autologous bone marrow transplantation is used increasingly i patients with breast cancer. (See e.g., Myers, et al. *Bone Marrow Transplantation*, 13:449–454 (1994); Ghalie, et al. Biology of Blood and Marrow Transplantation, 1:40–46 (1995); Bezwoda, et al. *J. Clin. Oncology*, 13:2483–2489 (1995); Kennedy, M. J., *J. Clin. Oncology*, 13:2477–2479 (1995); To, et al. *Blood*, 89:2233–2258 (1997). However, a high relapse rate after high dose chemotherapy is still observed, especially in women with metastatic breast cancer. Vahdat, L. and Antman, K. H. (1995) p. 802. Baltimore: Williams & Wilkins. In most cases, failure to eradicate disease by the treatment regimen is the cause of disease recurrence. However, there is strong evidence from gene marking studies that tumor cell contamination of the bone marrow cells can also contribute to recurrence in cancer patients. Brenner, et al., *Lancet*, 341:85–86 (1993); Brenner, et al. *Ann. N.Y. Acad. Sci.* 716:204–215 (1993); Deisseroth, et al. *Blood*, 83:3068–3076 (1994); Sharp, J. G., *J. Hematotherapy*, 5:519–524 (1996). Tumor cells can be detected not only in the bone marrow of patients having advanced breast cancer (20 to 70%) but also in the bone marrow of patients with localized breast cancer (20% to 45%) using sensitive immunocytochemical analysis or reverse transcriptase-polymerase chain reaction (RT-PCR) assays (See e.g., Berger, et al., *Am J Clin Pathol.*, 90:1–6 (1988); Mansi, et al., *Br. Med. J.* 295:1093–1096 (1987); Diel, et al., *J. Clin. Oncol.* 10:1534–1539 (1992); Porro, et al., *Cancer*, 61:2407–2411 (1988); Cote, et al., *J. Clin. Oncol.* 9:1749–1756 (1991).)

In order to avoid reinfusing the cancer cells into the patient undergoing high-dose chemotherapy in conjunction with autologous stem cell transplantation, practitioners have attempted to "purge" bone marrow cells of their contaminating tumor cells. various approaches for the ex vivo tumor cell purging of stem cell products have been developed. The use of monoclonal antibodies against membrane antigens with cytotoxic drugs, toxins, phototherapy, and biological modifiers or cytotoxic drugs can reduce tumor contamination by 1 to 3 logs (Seiden, et al., *J. Infusional Chemotherapy* 6:17–22 (1996)). However, purging using cytotoxic drugs often leads to delayed engraftment (Rummel, et al., *J. Hemotother*. 3:213–218 (1994)). The selection of CD34$^+$ hematopoietic progenitor cells has also been used to reduce tumor cell reinfusion, although demonstrating lower purging efficacy (1 to 2 logs). The clinical purging of breast cancer cells from bone marrow with 4-hydroperoxycyclophosphamide (4-HC) has been reported by Osborne et al. to improve clinical outcome (Osborne, et al., *Cancer Res.* 51:2706–2709 (1991)). However, the use of 4HC is not favored because 4HC is toxic to stem cells and delays neutrophil recovery. Furthermore, although 4HC results in approximately a 3 log purge of tumor cells, this is significantly less than the 5-log purge generally considered optimal to effectively purge tumor cells from a stem cell product. In another protocol, antibodies reactive with the tumor cells are conjugated to radioisotopes and have been demonstrated to purge tumor cells (Gibbons, et al). In this study, patients whose marrow was rendered "tumor free" following purging had a significantly improved survival compared to those whose marrow was not successfully purged.

Stem cell rescue, following myeloablative high dose chemotherapy with autologous bone marrow products has been predominately replaced with transplantation using mobilized peripheral blood stem cells (PSC). The use of PSC rescue results in a more rapid neutrophil recovery following high dose chemotherapy as compared to steady state autologous bone marrow transplantation (Bezwoda, et al., *J. Clin. Oncol.* 13:2483–2489 (1995); To, et al., *Blood* 89:2233–2258 (1997)). In addition it allows the use of stem cell products in patients with marrow aplasia due to radiation or who have extensive tumor contamination of the marrow.

Initially, it appeared the PSC products were free of tumor cells. However, more recent studies have demonstrated that cancer cells can also be detected in mobilized PSC products (Mapara et al. *Blood* 89:337–344 (1997)). This is a critical observation as gene marking studies have demonstrated that reinfused tumor cells can directly contribute to disease relapse and a poor clinical outcome. Whether all such contaminating tumor cells are capable of clonogenic growth is debatable and indeed it appears that only a subset of such tumor cells have clonogenic growth capacity. Nonetheless, in the cases of lymphoma, leukemia, breast cancer and neuroblastoma, at least some of the contaminating tumor cells have the capacity to grow clonogenically in vitro (Ross, et al., *Blood* 82:2605–2610 (1993)) as well in the patient. Although PSC products appear to have a reduced level of tumor cell contamination compared to the bone marrow, the potential for contaminating tumor cells to contribute to disease relapse is significant.

Seth et al. (*Cancer Research* 56:1346–1351 (1996)) disclosed that rAd-p53 may preferentially infect breast cancer cells compared to CD34+ mobilized peripheral stem blood cells. Chen et al. (*J. Clin. Invest.* 98:2539–2548 (1996)) disclosed a higher level of adenoviral-mediated reporter gene expression in breast cancer cells compared to bone marrow, peripheral blood and CD34+ cells, and disclosed the potential use of adenoviral vectors with tumor-selective promoters to detect and purge hematopoietic stem cell preparations.

As noted above, current protocols for the purging of stem cell populations have significant drawbacks. Thus, there is a need for new protocols for the effective purging of PSC products. This need and others are addressed by the instant invention.

SUMMARY OF THE INVENTION

The present invention provides a method to purge tumor cells from stem cell products using replication deficient adenovirus.

One aspect of the invention is a method of purging tumor cells from a stem cell product (SCP) having from approximately $2\times10^7$ to $3\times10^8$ nucleated cells/ml (NC/ml), the method comprising the co-incubation of the stem cell product with a replication-deficient, non-integrating adenovirus (rAd) at a particle number: nucleated cell (PN:NC) ratio of approximately 2,500:1 to 250,000:1 for approximately 4 to 24 hours. In some embodiments, the PC:NC ratio may be 25,000:1 to 250,000:1 or 2,500:1 to 25,000:1. In an embodiment the co-incubation time is approximately 4 to 16 hours. In an embodiment the co-incubation is performed in a total volume of about 0.1 to 2 ml and may be performed in a total volume of about 0.1 to 1 ml. In an embodiment the SCP may be derived from bone marrow, peripheral stem cells, or mobilized stem cells, and may be enriched for CD34+ cells. In an embodiment the tumor cells are carcinoma cells or hematopoietic tumor cells.

In an embodiment rAd comprises a DNA sequence encoding a cytotoxicity inducing factor (CIF), such as an apoptosis inducing tumor suppressor gene, a cytotoxic gene, a suicide gene, or a toxin gene. The rAd may be a recombinant adenovirus, such as a type 5 adenovirus.

Another aspect of the invention is a method of treating an individual having a disease which is treated by myeloablative therapy and stem cell rescue using a purged product the method comprising (a) the removal of a stem cell product from a patient in need of such treatment, (b) purging the stem cell product using a replication-deficient, non-integrating adenovirus to generate a purged product, and (c) reinfusing the purged product of (b) into the patient.

Another aspect of the invention is a kit for purging a stem cell product of tumor cells, the kit comprising a replication-deficient, nonintegrating adenovirus of a known total particle number/ml, and optionally containing at least one of a buffer for adjusting the concentration of the adenovirus, a buffer for adjusting the concentration of the adenovirus, and directions for use of the kit.

BRIEF DESCRIPTION OF THE DRAWINGS

FIG. 2 comprises FIGS. 2A and 2B and depicts the results of a clonogenic assay of breast cancer cell lines. Cells were infected with rAd-p53 (●) or rAd-β-gal (○) at increasing PN:NC ratios (425:1 to 68,000:1) in a volume of 50 microliters (2A) or 2 ml (2B) for 2 hours and assayed for clonogenic growth as described in Example 3 herein. Inhibition of colony formation is plotted as a percent of untreated cells. Bars represent the standard deviation. Data points denoted "@" demonstrate significant inhibition of clonogenic growth by rAd-p53 or rAd-β-gal vs. a PN:TC of 68,000:1. (P values <0.05). Data points denoted "&" demonstrate significant inhibition of clonogenic growth by rAd-p53 or rAd-β-gal in 50 microliters vs. in 2 ml; data points denoted "#" demonstrate a significant inhibition of clonogenic growth by rAd-p53 vs. by rAd-β-gal.

FIG. 5 comprises FIGS. 5A and 5B.

DEFINITIONS AND ABBREVIATIONS

Figure 1:
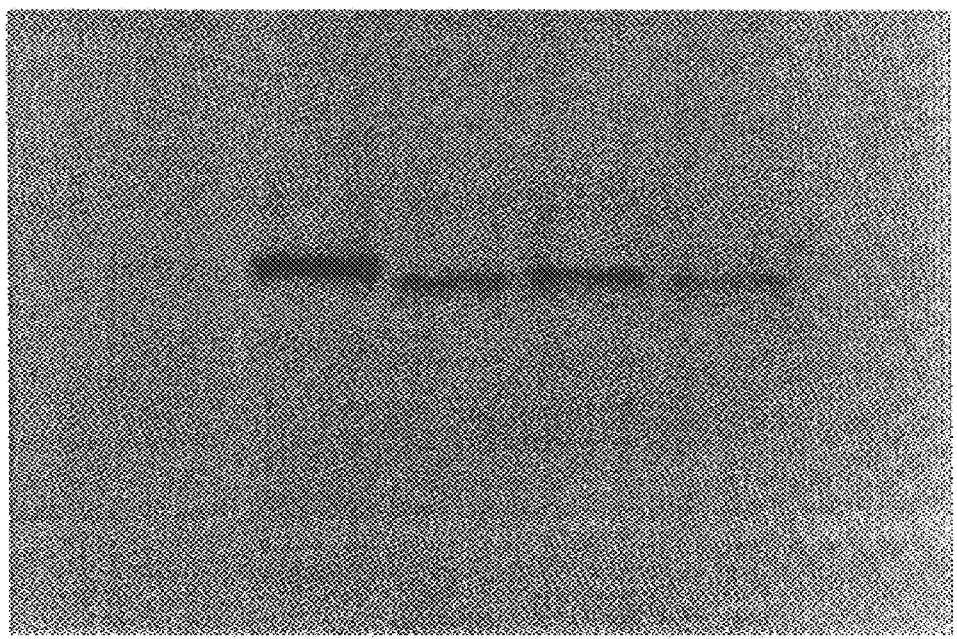
FIG. 1 is a representation of the expression of endogenous p53 in human tumor cell lines. Western blot detection was performed on cell lysates and endogenous p53 expression was measured by the monoclonal antibody Ab-7 as described in Example 2 herein.
Figures 3A, 3B:
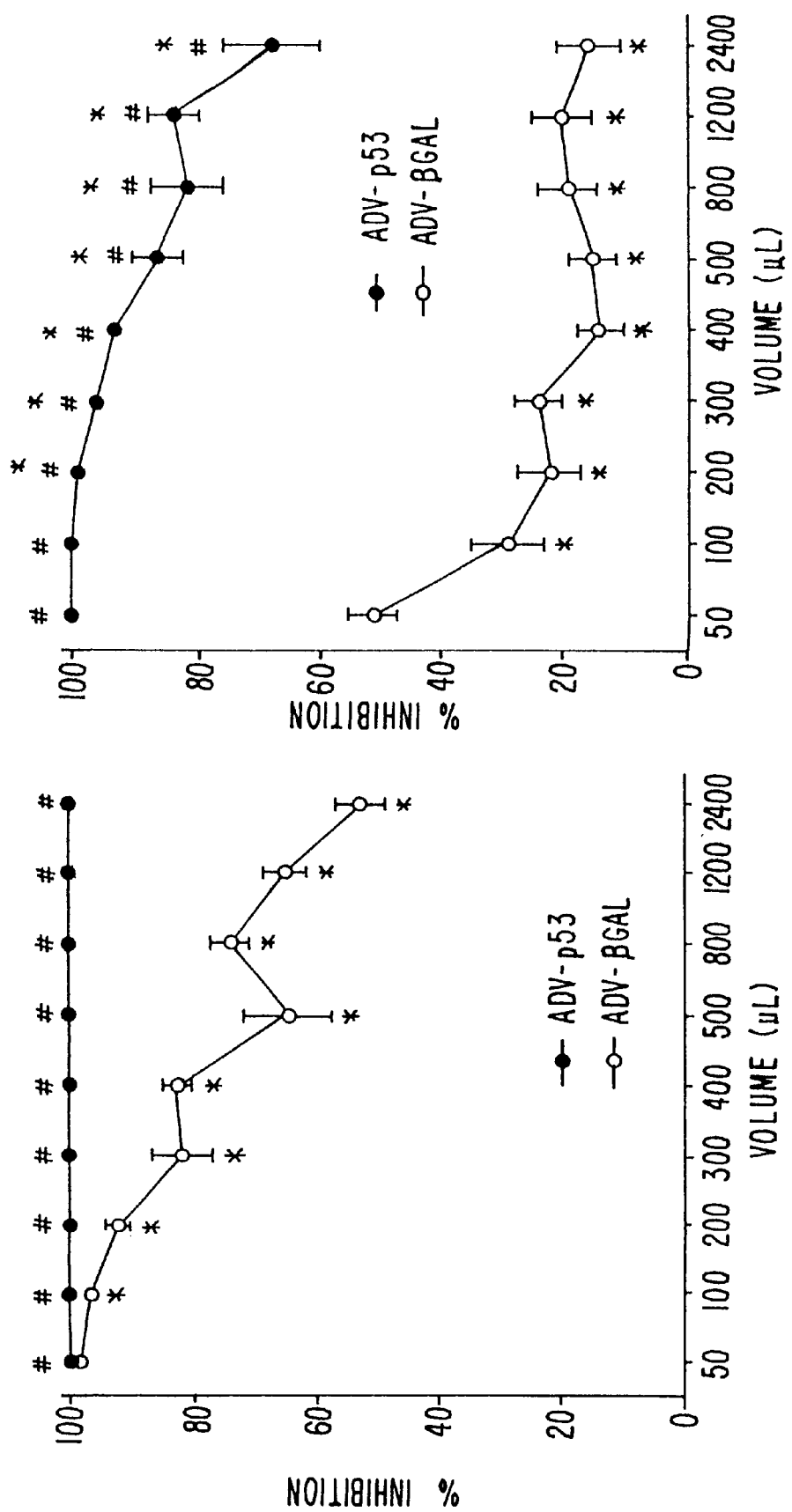
FIG. 3 comprises FIG. 3A and FIG. 3B and is a graphical representation of the effect of infection volume with rAd-p53 or rAd-β-gal on MDA-MB-231 (3A) or MDA-MB-435S (3B) cell lines. Cells were infected with rAd-p53 (●) or rAd-β-gal (○) at a PN:TC ratio of 42,500:1 for 2 hours in different volumes (50–2400 microliters) and assayed for clonogenic growth. The inhibition of colony formation is plotted as percent of untreated cells. Bars represent the standard deviation. The Figure demonstrates a significant inhibition of clonogenic growth by rAd-β-gal and an improved inhibition of clonogenic growth by rAd-p53 in varying volumes. Significant inhibition of clonogenic growth by rAd-p53 in varying volumes versus a volume of 50 microliters is indicated by "*". Significant inhibition of clonogenic growth by rAd-p53 versus by rAd-β-gal is indicated by "#". (P values <0.05).
Figures 4A, 4B:
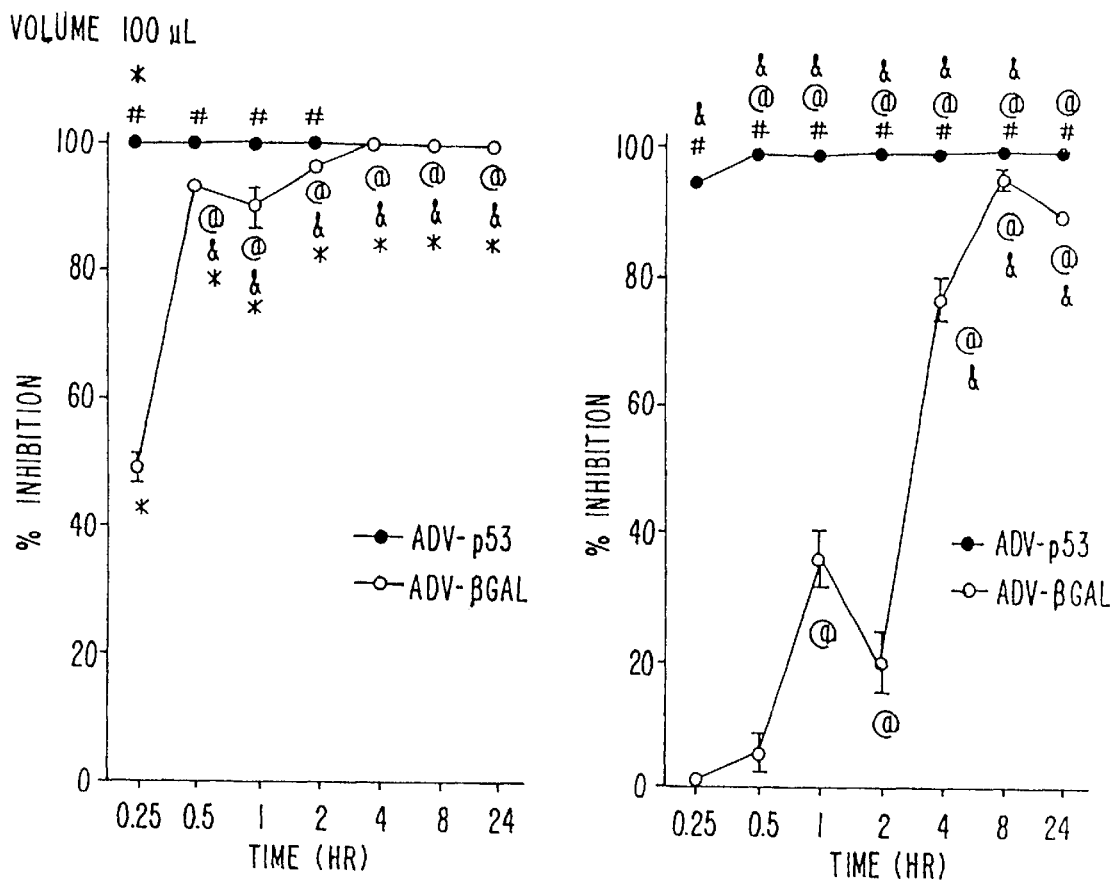
FIG. 4 comprises FIGS. 4A–4H and is a graphical representation of the effect of infection time with rAd-p53 or rAd-β-gal on MDA-MB-231 (4A–4D) or MDA-MB-435S (4E–4H) cells. Cells were infected with rAd-p53 (●) or rAd-β-gal (○) at a PN:TC ratio of 42,500:1 or 4,250:1 in a volume of 100 microliters or 2 ml for different infection times (0.25–24 hours) and assayed for clonogenic growth as described in Example 3 herein. Inhibition of colony formation is plotted as percent of untreated cells. Bars indicate standard deviation. The data points denoted "*" indicated significant inhibition of clonogenic growth by rAd-p53 or rAd-β-gal at a PN:TC ratio of 42,500:1 or 4,250:1 with incubation in 100 microliters. The data points denoted "#" indicate significant inhibition of clonogenic growth by rAd-p53 vs. by rAd-β-gal. The data points denoted "&" indicate significant inhibition of clonogenic growth by rAd-p53 or rAd-β-gal in a volume of 100 microliters vs. in a volume of 2 ml; The data points denoted "@" indicate significant inhibition of clonogenic growth by rAd-p53 or rAd-β-gal for varying time vs. for 0.25 hours. (P values<0.05).
Figure 4D:
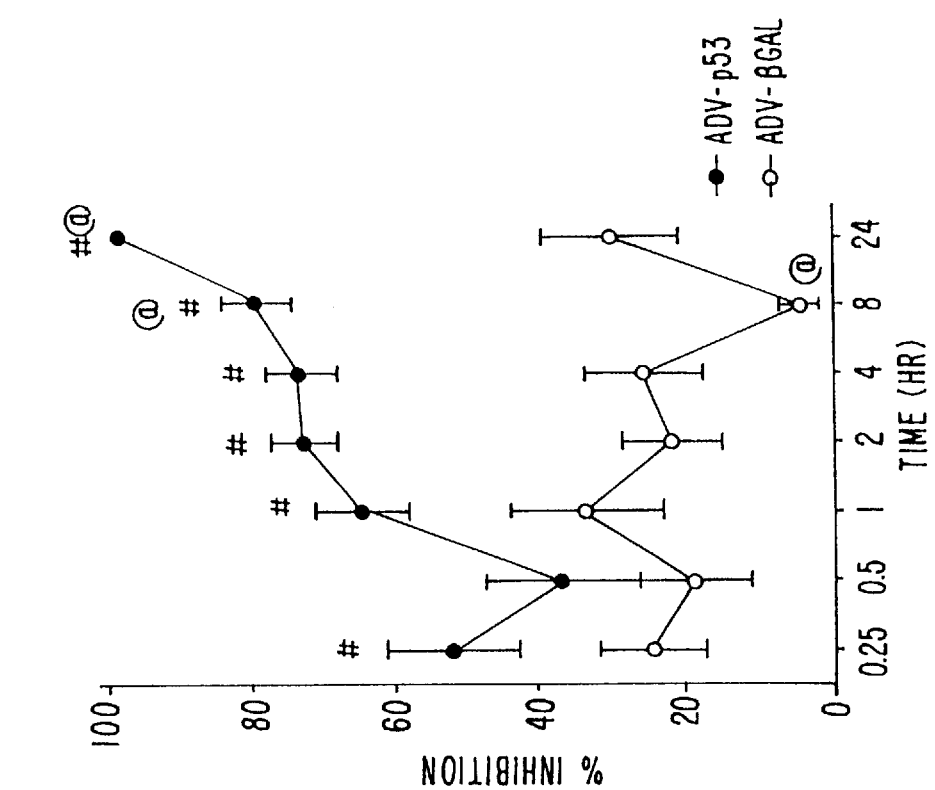
Figure 4C:
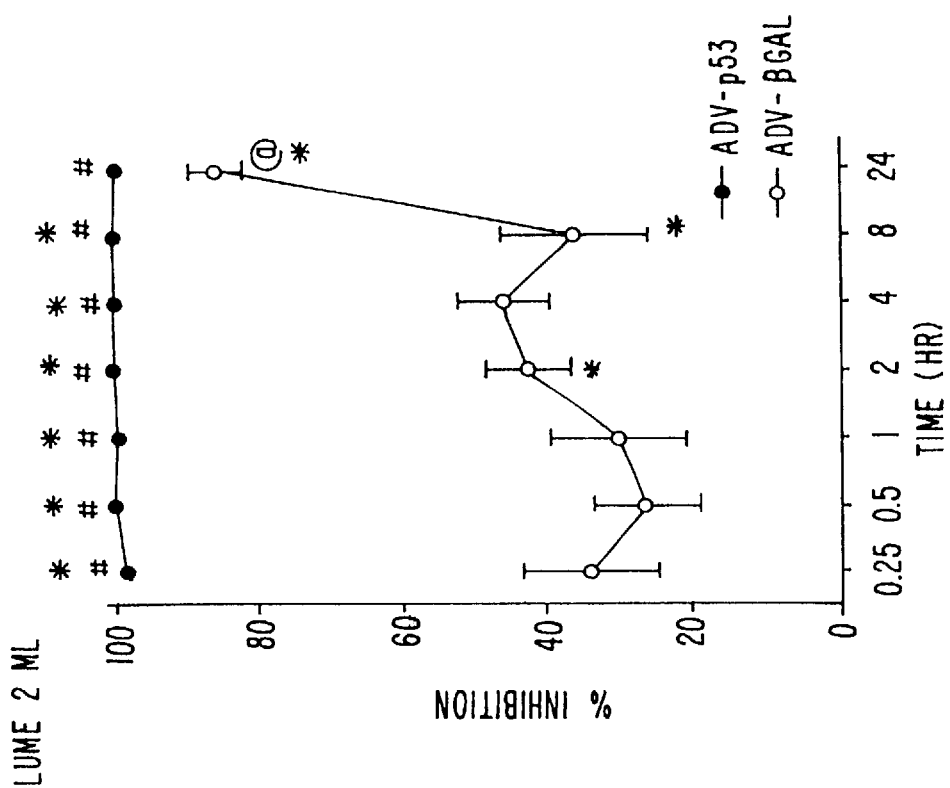
Figure 4F:
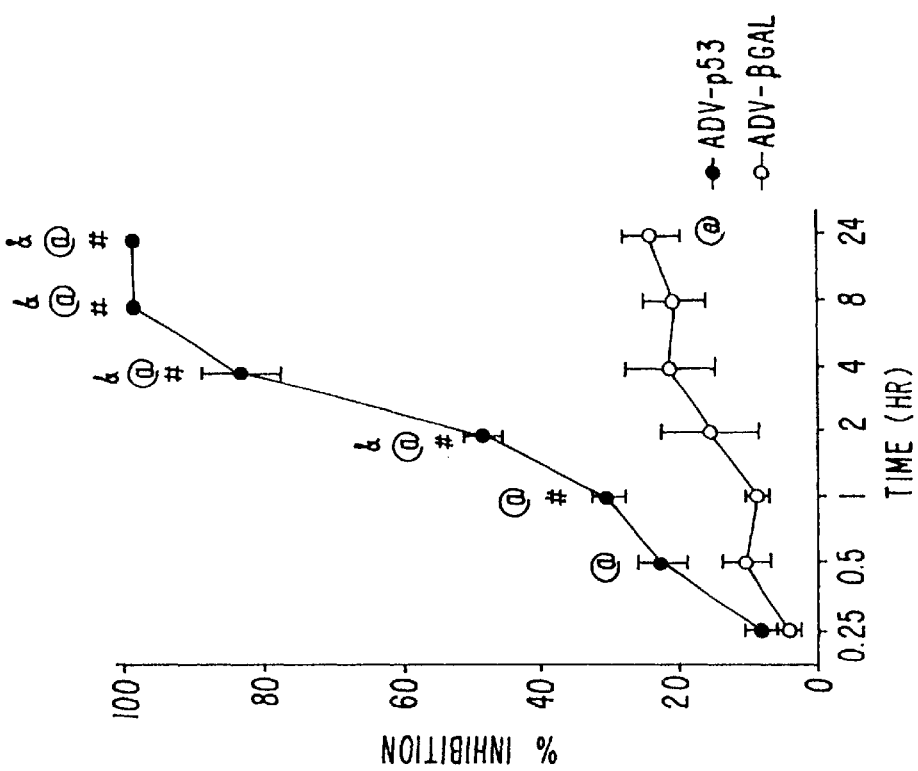
Figure 4E:
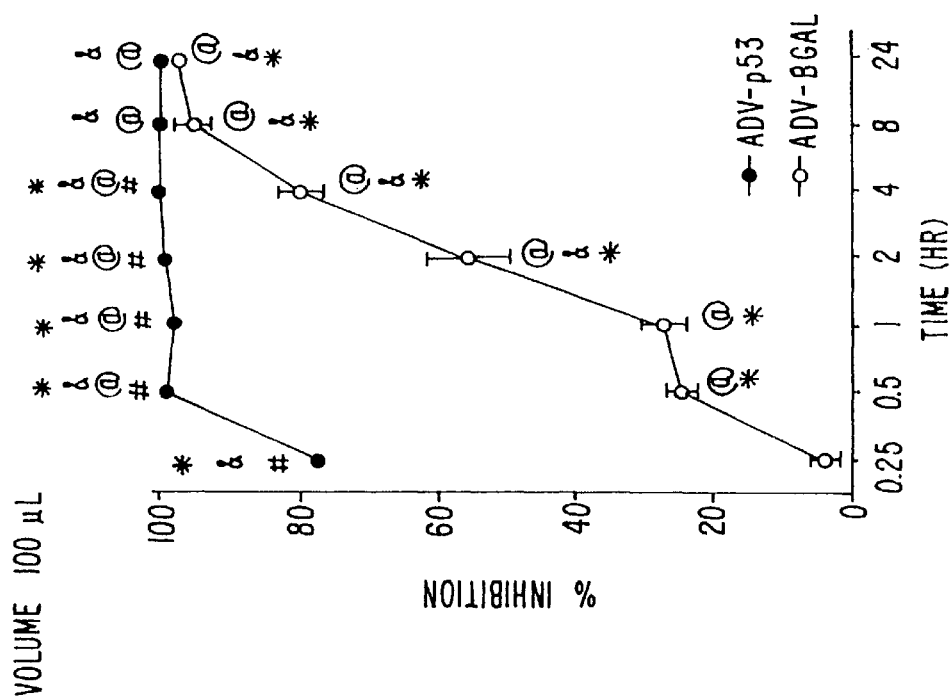
Figure 5A:
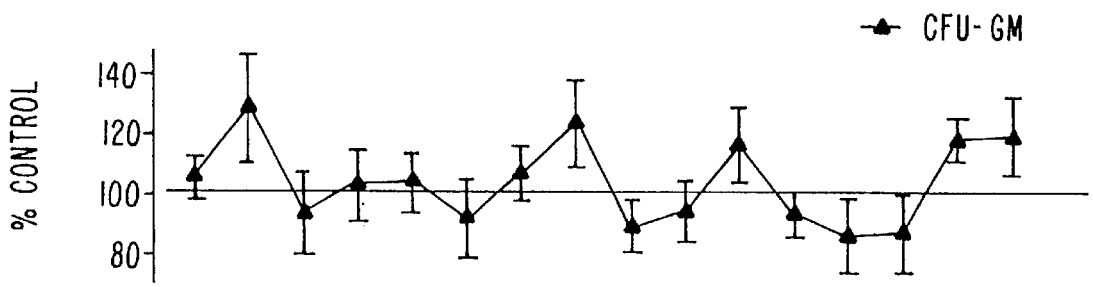
FIG. 5A is a graphical representation of the effect of rAd-p53 on CFU-GM (▲) of PSC product. Results are plotted as percent of control which was PSC and tumor cells incubated without rAd-p53.
Figure 5B:
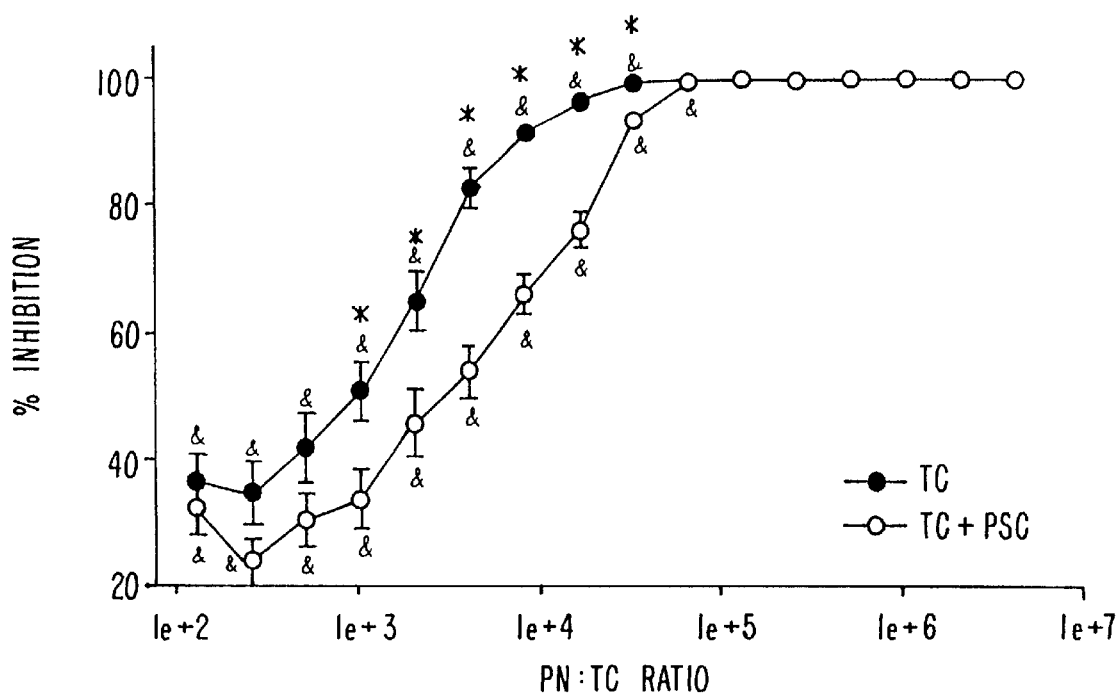
FIG. 5B is a graphical representation of the effect of PSC product on inhibition of clonogenic growth of MDA-MB-231 cell by rAd-p53. $8\times10^3$ tumor cells were infected with rAd-p53 at a PN:TC ratio of $1.1\times10^2$:1 to $4.25\times10^6$:1 in a volume of 100 microliters for 4 hours with (○) or without (●) $8\times10^6$ cells from PSC products from Non-Hodgkins Lymphoma ("NHL") patients and clonogenic tumor cell growth and CFU-GM quantified as described in Example 4 herein. Inhibition of colony formation is plotted as percent of untreated cells. This data demonstrates significant inhibition of clonogenic growth by rAd-p53 without PSC vs. with PSC (*) The data points marked with (&) demonstrate significant inhibition of clonogenic growth by rAd-p53 at varying PN vs. a PN:TC ratio of $4.25\times10^6$:1. (P values<0.05).

The term "Cytotoxicity Inducing Factor" (CIF) as used herein is defined as an agent which is cytotoxic to a cell to enhance the tumor cell killing capacity of the rAd allowing for a lower PN:NC ratio in a given volume at a given co-incubation. Examples of CIFs useful in the practice of the present invention include the products of (a) apoptosis inducing tumor suppressor genes (e.g., p53), (b) cytotoxic genes (e.g., tumor necrosis factor, interferon-alpha), (c) suicide genes (e.g., cytosine deaminase, thymidine kinase), (d) toxins such as pseudomonas endotoxin, ricin or diphtheria toxin subunits.

The term "myeloablative therapy" as used herein refers to the administration of chemotherapy and/or radiation therapy to a patient such that reinfusion of hematopoietic stem cells to the patient is required for patient survival after the chemotherapy and/or radiation therapy.

The term "NC" as used herein refers to nucleated cells including but not limited to hematopoietic cells, tumor cells, and the like.

The term "PN" as used herein refers to a total number of virus particles, for example, the total number of adenovirus particles used to treat the stem cell product in the methods of the invention.

The term "PSC" as used herein refers a peripheral blood stem cell, such as a stem cell circulating in the peripheral blood supply.

The term "purge" as used herein refers to the substantial elimination or removal of tumor cells from a population of normal cells, generally from an PSC. It is referred to in the context of a "x log purge" to indicate the effective reduction of tumor cells from the stem cell product in $1 \times 10^x$ cells.

The term "rAd" used herein refers to a replication-deficient, non-integrating adenovirus. In the preferred practice of the invention as exemplified herein, rAd is derived from a Type 5 adenovirus which has been modified such that the adenovirus is deficient in E1A and E1B viral protein functions.

The term "rAd-CIF" as used herein refers to an rAd vector further comprising a DNA sequence encoding a CIF or a functionally equivalent derivative thereof under control of a promoter operator region functional in the target cell.

The term "rAd-p53" as used herein refers to a recombinantly modified rAd containing a DNA sequence encoding the p53 tumor suppressor gene or a functionally equivalent derivative thereof under control of a promoter operator region functional in the target cell. In the preferred practice of the invention as exemplified herein, rAd-p53 is an adenovirus 5 derived vector wherein the DNA sequence encoding the E1A and E1B viral proteins have been replaced with the wild type p53 coding sequence under the control of the CMV promoter/operator.

The term "rAd-β-gal" as used herein refers to a recombinantly modified rAd containing a DNA sequence encoding the β-galactosidase gene under control of the CMV promoter.

The term "Stem Cell Product" (SCP) as used herein refers to a population of hematopoietic, progenitor, and stem cells capable of reconstituting the long term hematopoietic function of a patient who has received myeloablative therapy. A SCP is normally obtained by apheresis of mobilized or non-mobilized peripheral blood, or a manipulated product from any of the above.

The term "TC" as used herein refers to a tumor cell, i.e., a cell which exhibits a neoplastic phenotype.

DETAILED DESCRIPTION OF THE INVENTION

The present invention provides a method to purge tumor cells from stem cell products using a replication deficient adenovirus, the method comprising the co-incubation of the stem cell product with a rAd at a concentration, time and volume sufficient to eliminate the tumor cells from the population

Obtaining the Stem Cell Product

In the clinical setting, stem cell products (SCP) are obtained by various means. Bone marrow cells are generally obtained by multiple penetrations into the bone marrow cavity using a large gauge needle through which the bone marrow cells are extracted. Peripheral stem cells are generally isolated from mobilized peripheral blood by the differential centrifugation technique known as apheresis. Apheresis is achieved through the use of known procedures using commercially available apheresis apparatus such as but not limited to the COBE® Spectra™ Apheresis System (commercially available from COBE International, 1185 Oak Street, Lakewood, Colo., USA).

In many instances it is preferred to mobilize stem cells from the marrow into the peripheral blood to increase the frequency of stem cells. This is generally achieved by the use of growth factors such as GM-CSF or G-CSF. Although chemotherapy with or without growth factor expansion will mobilize stem cells to the periphery, growth factor support results in a reduced incidence of myelosuppression compared to chemotherapy alone. The cells are collected by one or more cycles of apheresis until a predetermined number of nucleated or $CD34^+$ cells are harvested. In most clinical conditions, the minimum number of nucleated cells from a peripheral stem cell product to be reinfused is approximately $6.5 \times 10^8$ cells/kg of patient bodyweight. It is generally perceived that minimum of $1.4 \times 10^6$ of $CD34^+$ cells per kilogram of bodyweight is required for successful hematopoietic recovery.

Further, the progenitor and stem cells may be enriched and tumor cell contamination reduced by antibody facilitated isolation using methods well known in the art and materials commercially available such as but not limited to the CEPRATE® SC Stem Cell Concentration System (CellPro, Inc., Bothwell, Wash.) or the Miltenyi Progenitor Cell Isolation Kit (Miltenyi Biotec, Inc., Sunnyvale, Calif.). The SCP to be treated in accordance with the method of the present invention may be enriched by these methods in conjunction with the present treatment method. In addition to reducing tumor cell contamination, the enrichment of $CD34^+$ cells results in the infusion of fewer cells and decreased levels of cryoprotectant which reduces of the toxicity of the treatment strategy of the invention.

The isolated SCP is then generally cryopreserved using a cryopreservative such as Pentastarch (generic) and/or dimethyl sulfoxide ("DMSO") and stored in liquid nitrogen according to known procedures. Following high dose chemotherapy, the cells are thawed and reinfused to the patient to restore hematopoietic function. The purging method of the present invention may be performed before or after freezing, preferably before.

Determining Tumor Cell Contamination

Tumor cell contamination in the SCP may be determined, for example, by routine pathological examination. The majority of carcinomas result in stem cell products with tumor cells being less than one percent of total nucleated cells. However, in multiple myelomas or other hematological malignancies, this may be higher (in the range of 30–50%). In such instances, an increase in PN ratio may be required to achieve to achieve successful treatment. As CD34+ cells are relatively ineffectually infected by rAd, total PN used for treatment of the SCP may be increased up to approximately one log higher in such instances.

rAd Purging Protocol

In order to achieve clinically effective bone marrow purging, it is generally considered necessary to effect a 3 log purge (99.9% tumor cell killing) with an optimum of approximately a 5 log purge (99.999% tumor cell killing). In order to achieve this purging of tumor cells from a stem cell product population using rAd, the opportunity for rAd particles to contact the tumor cell must be facilitated. As the ability of an rAd particle to infect a given cell requires both contact with the target cell as well as successful incorporation of the virus into the cell is largely a diffusion driven process, three factors must be balanced to achieve optimal purging of the SCP: (1) volume (2) co-incubation time and (3) the PN:NC ratio.

PN:NC Ratio

This is the ratio of total rAd particles to nucleated cells in the sample. The number of nucleated cells is determined by conventional procedures such as hemacytometer or mechanical enumeration on commercially available equipment such as the Coulter® Gen-S™ hematology system (Beckman Coulter, Inc. Miami, Fla.). In keeping with the diffusive nature of the infection process, higher PN:NC ratios permit shorter co-incubation times and/or larger co-incubation volumes. In the absence of abnormally high tumor burden, the preferred PN:NC ratio is about 25,000 rAd viral particles per nucleated cell in a co-incubation volume of about 1 ml. For example, in a typical apheresis SCP containing approximately $2 \times 10^8$ nucleated cells/ml (cellularity adjusted, for example, using the patient's plasma) one would generally co-incubate the SCP with $5 \times 10^{12}$ rAd particles/ml for a four hour co-incubation. In conditions of heavier tumor cell contamination, it may be useful to increase the PN to approximately $2 \times 10^{13}$ PN/ml for a four hour incubation.

Volume

A smaller co-incubation volume typically results in greater cytotoxicity than a larger volume at a given PN:NC ratio. Thus, a smaller volume can allow the use of fewer total rAd particles and/or shorter incubation times as the frequency of a successful interaction between virus and tumor cell is increased. Typically, one would expect to incubate a stem cell product at approximately $1-2 \times 10^8$ nucleated cells/ml. Although this will typically range from $2 \times 10^7$ to $3 \times 10^8$ cells/ml, by controlling co-incubation volume it is possible to effectively purge a population of cells of tumor cells without significantly reducing progenitor or stem cell populations.

Time

The longer the exposure of the cell to the adenovirus, the more effective cell killing is achieved as there is a greater opportunity for interaction between a given rAd particle and the target tumor cell. Longer co-incubation time permits the use of lower PN:NC ratios and/or larger co-incubation volumes. 24 hours is generally considered the maximum clinically practical time to effectuate the purging protocol, although longer exposure times are possible. Depending on the foregoing factors of reaction, volumes and PN:NC ratio, 2 hours is probably the minimum time necessary to achieve effective stem cell purging. In the preferred practice of the invention as exemplified herein, a co-incubation time of from 4 to 16 hours is preferred. The co-incubation is preferably performed at ambient temperature, more preferably at about 37° C.

To demonstrate the effects of rAd at various times of exposure, the clonogenic growth of MDA-MB-231 and -435S were compared at two different PN:TC ratios (42,500:1 or 4,250:1) in an incubation volume of 100 microliters or 2 ml over varying times in order to assess the optimal time exposure. In cells treated with rAd-p53 or rAd-β-gal for 0.25 to 24 hours (FIG. 4) MDA-MB-231 had a complete loss of clonogenic growth by rAd-p53 at all incubation times, at the high concentration of rAd-p53 (PN:TC ratio of 42,500:1) and in a volume of 100 microliters. In contrast, the lower concentration of rAd-p53 (volume of 2 ml and with a PN:TC ratio of 4,250:1) revealed an incubation time dependent loss of clonogenic growth. At the high concentration (PN:TC ratio of 42,500:1 in 100 microliters), rAd-p53 also induced a total loss of clonogenic growth of MDA-MB-435S when incubated for more than 0.5 hours. But when the rAd-p53 concentration was reduced (2 ml co-cultures), the maximum loss of clonogenic growth of MDA-MB-435S was approximately 80%. rAd-β-gal also inhibited clonogenic growth depending on incubation time in a volume of 100 microliters.

Removal of Excess Virus

Although the concentration of adenovirus utilized in the practice of the present invention is tolerated by patients based on clinical experience, in some instances it may be useful to reduce the level of the virus. Excess virus may be removed from the stem cell product prior to reinfusion by chromatographic procedures by washing in an apheresis unit or other techniques.

Inclusion of Cytotoxicity Inducing Factor in rAd

In the preferred practice of the invention as exemplified herein, the rAd vector further comprises a DNA sequence encoding an cytotoxicity inducing factor (CIF) to enhance the tumor cell killing capacity of the rAd, allowing for a lower PN:NC ratio in a given volume at a given co-incubation. Examples of CIFs useful in the practice of the present invention include the products of (a) apoptosis inducing tumor suppressor genes (e.g., p53, Rb, BRCA-1), (b) cytotoxic genes (e.g., tumor necrosis factor, interferon-alpha), (c) suicide genes (e.g., cytosine deaminase, thymidine kinase), (d) toxins such as pseudomonas endotoxin, ricin or diphtheria toxin subunits. When the rAd vector contains a CIF, it is possible to reduce the PN administered in a given volume at a given time by approximately one order of magnitude.

In the most preferred practice of the invention as exemplified herein, the use of rAd-p53 to purge a stem cell product having a concentration of approximately $2 \times 10^8$ cells/ml for a co-incubation period of approximately 4 hours allowed a lower PN:NC ratio to achieve effective purging. Loss of p53 function is known to be associated with tumor cell resistance to antitumor therapy (Lowe, et al., *Cell* 957–967 (1993); Fujiwara, et al., *Cancer Res.* 54:2287–2291 (1994)). Thus, p53 mutations which are observed in tumor cells, may limit the effect of "traditional" purging techniques, while high levels of wild type p53 production can suppress cancer cells with altered p53 expression (Harris, et al., *Cancer Gene Ther.* 3:121–130 (1996); Katayose, et al., *Clin. Canc. Res.* 1:889–897

(1995)). As indicated in the data presented herein, a rAd-p53 particle concentration of $1\times10^{10}$ PN/ml was sufficient to achieve at least a 3 log purge of tumor cells from stem cell products under the conditions specified. Further, rAd-p53 purging appears to be less toxic to progenitor cells than most other techniques of cytotoxic purging strategies (Meeker et al., *Clin. Cancer Res.* 3:357–364 (1997)). The relative resistance of stem cell products (Watanabe, et al., *Blood* 87:5032–5039 (1996); Watanabe, et al., *Leukemia & Lymphoma* in press (1998); Chen, et al., *J. Clin. Invest.* 98:2539–2548 (1996); Wroblewski, et al., *Blood* 89:4664–4665 (1997)) to replication-deficient recombinant human adenoviruses suggests that non-specific cytotoxicity of adenovirus is limited to tumor cells and that rAd or rAd-p53 can purge tumor cells in PSC effectively (FIG. 4).

It has been reported that cell lines containing wild type p53 are not growth inhibited by transduction with rAd-p53 as compared to cell lines possessing mutant p53 (Harris, et al., *Cancer Gene Therapy* 3:121–130 (1996); Katayose, et al., *Clin. Canc. Res.* 1:889–897 (1995)). However, rAd-p53 transduction of the wild type p53 gene into tumor cells can suppress cell growth by the over-expression of wild type p53 protein or by non-specific cytotoxic mechanisms (Katayose, et al., *Clin. Canc. Res.* 1:889–897 (1995)). A 90% loss of clonogenic growth of MCF-7 cells was observed in a volume of 100 microliters at a MOI of 200:1 following 2 hours incubation time by Wroblewski, et al. (Wroblewski, et al., *Blood* 89:4664–4665 (1997)). However, as previously discussed, a 90% loss of clonogenic growth is not a clinically acceptable level of purging. As indicated in the data presented, the method of the present invention achieves clinically acceptable purging of p53+ tumor cell lines in contrast to previously reported procedures.

Inclusion of Multiple CIFs or Elements Which Enhance CIF Effect

As indicated above, the effectiveness of an rAd in eliminating tumor cells can be enhanced by the inclusion of a sequence to effect the expression of an CIF in a given cell. It is also of benefit to include in such vectors multiple transgenes for both the CIF as well as agents which enhance the effect of the CIF. Examples of such combinations include but are not limited to p16 and p53, p53 and tk, p53 and p21.

Other transgenes may also be included in the adenovirus construct, such as tumor suppressor genes such as but not limited to RB, BRCA-1, etc.

Formulations

The rAd vectors may be admixed with conventional pharmaceutically acceptable carriers. In the formulations of the invention, a buffer containing an rAd vector may be any pharmaceutical buffer such as phosphate buffered saline or sodium phosphate/sodium sulfate, Tris buffer, glycine buffer, sterile water and other buffers known to the ordinarily skilled artisan such as those described by Good et al. (1966) Biochemistry 5:467. The pH of the buffer in the pharmaceutical composition comprising the an rAd vector may be in the range of 6.4 to 8.4, preferably 7 to 7.5, and most preferably 7.2 to 7.4.

The compositions of this invention may additionally include a stabilizer, enhancer or other pharmaceutically acceptable carriers or vehicles. A pharmaceutically acceptable carrier can contain a physiologically acceptable compound that acts, for example, to stabilize the rAd vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of pharmaceutically acceptable carrier, depends on the route of administration and the particular physiochemical characteristics of the rAd vector. Examples of carriers, stabilizers or adjuvants can be found in Martin, *Remington's Pharm. Sci.*, 15th Ed. (Mack Publ. Co., Easton, Pa. 1975), incorporated herein by reference.

Furthermore, the rAd vectors of the invention may be used in conjunction with other agents which enhance their uptake into the tumor cells or provide targeting specificity to tumor cells. Examples of such delivery-enhancing agents are detergents, alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol. Acetates such as acetic acid, gluconic acid, and sodium acetate are further examples of delivery-enhancing agents. Hypertonic salt solutions like 1M NaCl are also examples of delivery-enhancing agents. Examples of surfactants are sodium dodecyl sulfate (SDS) and lysolecithin, polysorbate 80, nonylphenoxypolyoxyethylene, lysophosphatidylcholine, polyethylenglycol 400, polysorbate 80, polyoxyethylene ethers, polyglycol ether surfactants and DMSO. Bile salts such as taurocholate, sodium tauro-deoxycholate, deoxycholate, chenodesoxycholate, glycocholic acid, glycochenodeoxycholic acid and other astringents like silver nitrate may be used. Heparin-antagonists like quaternary amines such as protamine sulfate may also be used. Cyclooxygenase inhibitors such as sodium salicylate, salicylic acid, and non-steroidal anti-inflammatory drug (NSAIDS) like indomethacin, naproxen, diclofenac may be used.

Detergents include anionic, cationic, zwitterionic, and nonionic detergents. Exemplary detergents include but are not limited to taurocholate, deoxycholate, taurodeoxycholate, cetylpyridium, benalkonium chloride, ZWITTERGENT®3–14 detergent, CHAPS (3-[(3-Cholamidopropyl)dimethylammoniol]-1-propanesulfonate hydrate, Aldrich), Big CHAP, Deoxy Big CHAP, TRITON®-X-100 detergent, C12E8, Octyl-B-D-Glucopyranoside, PLURONIC®-F68 detergent, TWEEN® 20 detergent, and TWEEN® 80 detergent (CALBIOCHEM® Biochemicals).

The concentration of the delivery-enhancing agent will depend on a number of factors known to one of ordinary skill in the art such as the particular delivery-enhancing agent being used, the buffer, pH, target cell and mode of administration. The concentration of the delivery-enhancing agent will be in the range of 1% to 50% (v/v), preferably 10% to 40% (v/v) and most preferably 15% to 30% (v/v) Preferably, the detergent concentration in the final formulation administered to the tumor cells is about 0.5–2X the critical micellization concentration (CMC).

In order to facilitate the improved gene transfer for rAd vector formulations comprising commercial Big-CHAP preparations, the concentration of Big CHAP will vary based on its commercial source. When the Big CHAP is sourced from CALBIOCHEM®, it is preferred that the concentration be in a range of 2 to 10 millimolar. More preferred is 4 to 8 millimolar. Most preferred is approximately 7 millimolar.

When the Big CHAP is sourced from Sigma, it is preferred that the concentration of Big CHAP be in a range of 15 to 35 millimolar. More preferred is 20 to 30 millimolar. Most preferred is approximately 25 millimolar.

In a further embodiment of the invention, delivery-enhancing agents having Formula I are provided:

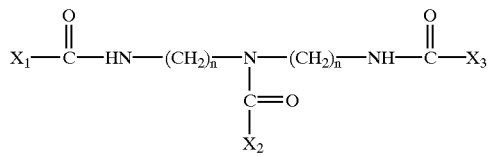

wherein n is an integer from 2–8, $X_1$ is a cholic acid group or deoxycholic acid group, and $X_2$ and $X_3$ are each independently selected from the group consisting of a cholic acid group, a deoxycholic acid group, and a saccharide group. At least one of $X_2$ and $X_3$ is a saccharide group. The saccharide group may be selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups. In one preferred embodiment, the compounds of the present invention have the Formula II:

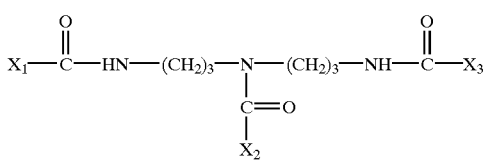

wherein $X_1$ and $X_2$ are selected from the group consisting of a cholic acid group and a deoxycholic acid group and $X_3$ is a saccharide group.

These compounds are preferably used in the range of about 0.002 to 2 mg/ml, more preferably about 0.02 to 2 mg/ml, most preferably about 0.2 to 2 mg/ml in the formulations of the invention. Most preferred is approximately 2 mg/ml.

Phosphate buffered saline (PBS) is the preferred solubilizing agent for these compounds. However, one of ordinary skill in the art will recognize that certain additional excipients and additives may be desirable to achieve solubility characteristics of these agents for various pharmaceutical formulations. For example, the addition of well known solubilizing agents such as detergents, fatty acid esters, surfactants may be added in appropriate concentrations so as to facilitate the solubilization of the compounds in the various solvents to be employed. When the solvent is PBS, a preferred solubilizing agent is Tween 80 at a concentration of approximately 0.15%.

These delivery-enhancing compounds may be used alone, in combination with each other, or in combination with another delivery-enhancing agent.

Furthermore, virus-cell contact may be enhanced by mixing of the virus and cells during infection. This can be done during apheresis itself or afterwards. Mixing can be accomplished by stirring, agitation, rocking, etc.

Methods of Administration

The methods of the present invention may also be practiced alone or in combination with additional agents to preserve cells ex vivo. For example, the procedure may be practiced in the presence of hematopoietic growth factors. Examples of preferred hematopoietic growth factors include IL-3, stem cell factor (SCF) and flt-3 ligand to increase stem cell survival, although any hematopoietic growth factor which reduces progenitor/stem cell apoptosis may be used.

Diseases Amenable to Treatment

The method of the present invention may be used in the treatment of all forms of cancer in conjunction with any autologous stem cell rescue protocol. This method is particularly useful in treating breast cancer, and other carcinomas such as prostate, ovarian, lung colon, neuroblastomas as well as hematopoietic origin tumors such as lymphomas and leukemias.

Clinically, mutations of wild-type p53 are observed in 30–50% of breast cancer patients and an additional 30% have nonfunctional, wild type p53 (Ozbun, et al. (1995) Cancer Res., 66: 71–141). As breast cancer cell lines have a high number of adenovirus receptors that facilitates adenovirus mediated gene transfer (Seth, et al., Cancer Res. 56:1346–1351 (1996); Blagosklonny, et al., Int. J. Cancer 67:386–392 (1996)) by receptor mediated endocytosis (Seth, et al., Virus Attachment and Entry Into Cells pp. 191–195 (1986); Seth, et al., J. Virol. 68:933–940 (1994)) and adenovirus infection has been shown to result in transgene expression in breast cancer cells at a higher level than in hematopoietic stem cell products (Harris, et al., Cancer Gene Therapy 3:121–130 (1996); Chen, et al., J. Clin. Invest. 98:2539–2548 (1996); Wroblewski, et al., Blood 89:4664–4665 (1997)), the method of the present invention is particularly useful in the purging of breast cancer cells from stem cell products.

The present invention further provides a kit comprising the pharmaceutical formulation and elements to facilitate the practice of the method of the present invention. An exemplary kit comprises a replication-deficient, nonintegrating adenovirus of a known total particle number/ml, and optionally containing at least one of a buffer for adjusting the concentration of the adenovirus, a buffer for adjusting the concentration of the adenovirus, and directions for use of the kit.

The following examples are intended to illustrate, not limit the scope of this invention.

EXAMPLES

Statistical Analysis

In all experiments, the cells were plated in triplicate, and each experiment was repeated 2–3 times (total N=6–9). Means and standard error of means (SEM) were obtained from pooled data. Statistical analyses were performed by two tailed Student's t-test using SPSS (commercially available from SPSS Inc.) for Windows® (Microsoft Corporation, Seattle, Washington) A p value less than 0.05 was considered to indicate statistical significance.

Example 1

Construction of Recombinant Adenoviruses

Replication-deficient adenovirus vectors encoding E. coli β-galactosidase (rAd-β-gal) or p53 (rAd-p53) were prepared, purified, and titered in substantial accordance with the teaching of Wills, et al. (1995) *Hum. Gene Ther.* 5: 1079–1088 and Huyghe, et al. (1995). *Hum. Gene Ther.* 6: 1403–1416. Briefly, in the adenovirus vectors, a portion of the E1a and E1b region of the human adenovirus type 5 was replaced with the lacZ or p53 gene under the transcriptional control of a human cytomegalovirus (CMV) promoter. rAd-β-gal and rAd-p53 were produced in the 293 human embryonic kidney cell line and purified by ultracentrifugation or column chromatography. Titers of the viral stocks used were $1.1–5.8 \times 10^{10}$ infectious units (IU)/ml by dilution assay on 293 cells and $4.6–10 \times 10^{11}$ particle numbers (PN)/ml rAd-β-gal or rAd-p53 in a buffer solution of 2% sucrose and 2 mM $MgCl_2$ stored at $-70°$ C.

Example 2

Preparation of Human Breast Cancer Cell Lines

In order to evaluate rAd-p53 efficacy, several human breast cancer cell lines having wild type and various p53 mutations were prepared (see Table 1 below). MDA-MB-231, -435S and -468, SK-BR-3 and MCF-7 human breast cancer cell lines were obtained from the ATCC (Rockville, Md.). MDA-MB-231 and -435S and SK-BR-3 cells were maintained in DME containing 50% HAM F-12, 10% fetal bovine serum (FBS), 1% glutamine and 40 micrograms/ml of gentamicin at 37° C., 5% $CO_2$. MDA-MB-468 cells were maintained in Kaighn's DME containing 50% HAM F-12, 10% fetal bovine serum (FBS), 1% glutamine, 40 micrograms/ml of gentamicin and 0.2 IU/ml of insulin at 37° C., 5% $CO_2$. MCF-7 cells were maintained in DME containing 10% fetal bovine serum (FBS), 1% glutamine and 40 micrograms/ml of gentamicin at 37° C., 5% $CO_2$.

Expression of endogenous p53 was graded on a semi-quantitative scale (+, ++, +++) following in accordance with the following procedure. Cells were lysed in buffer containing 50 mmol/l Tris-HCl, pH 7.5, 250 mmol/l NaCl, 0.1% NP-40, 50 mmol/l NaF, 5 mmol/l EDTA, 10 micrograms/mL aprotinin, 10 micrograms/ml leupeptin, and 1 mmol/l PMSF. After a freeze/thaw cycle and centrifugation at 12,000×g, the supernatants were harvested. Ten micrograms of each protein lysate were electrophoresed on a 12% Tris-glycine gels (commercially available from Novex, San Diego, Calif.). The proteins were transferred onto 0.2 micron nitrocellulose membranes and blocked with a 0.5% casein solution for 1 hour. The membrane was incubated in the presence of the Ab-7 anti-p53 polyclonal antibody (commercially available from Oncogene Research Products, Cambridge, Mass.), washed, and incubated in rabbit-anti-sheep Ig HRP (commercially available from Boehringer Mannheim, Arlington Heights, Ill.). p53 protein was detected by enhanced chemiluminescence utilizing an ECL kit commercially available from (commercially available from Amersham, Indianapolis, Ind.). The results of p53 expression for each cell line studied are shown in Table 1.

TABLE 1

Endogenous expression of p53 protein in human breast cancer cell lines

| Cell Line | Western* | P53** |
|---|---|---|
| MCF-7 | – | wild type |
| MDA-MB-468 | +++ | 273 Arg to His |
| SKBR-3 | + | 175 Arg to His |

TABLE 1-continued

Endogenous expression of p53 protein in human breast cancer cell lines

| Cell Line | Western* | P53** |
|---|---|---|
| MDA-MB-231 | ++ | 280 Arg to His |
| MDA-MB-435S | +++ | 266 Gly to Glu |

*Measure of endogenous p53 protein expression by the antibody Ab-7
**See (Harris, et al., Cancer Gene Therapy 3:121–130 (1996))

Example 3

Purging With rAd

Cells prepared in accordance with the teaching of Example 2 above were harvested from 30–50% confluent tissue culture flasks and adjusted to a concentration of $5 \times 10^4$ cells/ml. rAd-p53 or rAd-β-gal was added at the designated virus ratio (particle number:tumor cell; PN:TC) in a measured volume of complete media in round bottom polypropylene tubes (obtained from Becton Dickinson, Lincoln Park, N.J.). Cells were incubated at 37° C., 5% $CO_2$, until the number of cells was sufficient to result in 50 to 100 colonies (dependent on the cell line). The cells were cultured in 60 mm round tissue culture plates (n=3) in a volume of 5 ml complete media at 37° C., 5% $CO_2$. The plates were incubated for a sufficient time to allow for colony formation (10–18 days dependent on the cell line). The colonies were fixed and stained for one hour with a 70% ethanol solution containing 0.1% methylene blue, and the colony number was counted using Biotran automatic count totalizer (commercially available from New Brunswick Scientific Co. Inc., Edison, N.J.). Percent inhibition was defined as (number colonies in treated cultures/number colonies in control cultures) ×100.

After incubation of tumor cells and rAd-p53, the PMNC were harvested by centrifugation and the numbers of cells was analyzed using a System 9000 Hematology Series Cell counter (commercially available from Serono-Baker Diagnostic Inc., Allentown Pa.). Colony forming units-granulocyte/macrophage (CFU-GM) were quantitated in a soft agar culture system in substantial accordance with the teaching of Watanabe, et al. *Blood*, 87: 5032–5039 (1996). $1 \times 10^5$ PMNCs were cultured in 1 ml of 0.3% agar-IMDM containing 25% FBS, 100 units/ml penicillin, 100 micrograms/ml streptomycin, and $5 \times 10^{-5}$ M 2-mercaptoethanol (2-ME). 200 units/ml rHu IL-3, 200 units/ml rHu GM-CSF, and 200 units/ml rHu G-CSF were added as sources of stimulating activity. The cells were plated in 35 mm plates and incubated at 37° C. in a humidified atmosphere containing 5% $CO_2$ in air. After a 14 day incubation, colonies consisting of 40 cells or more were counted under an inverted microscope.

As indicated by the data presented in FIG. 2, all cell lines were sensitive to p53 inhibition of clonogenic growth when infected with rAd-p53. Even low rAd-p53 concentrations could totally inhibit clonogenic growth of MDA-MB-231 in co-cultures for 24 hours. In previous studies, MDA-MB-231 cells were co-cultured with rAd-p53 resulting in a 50% growth inhibition at (a) a MOI of 1:1 (100 microliters for 2 hours) (Seth, et al.(1996) *Cancer Res.* 56: 1346–1351) or (b) a MOI of 12:1 (200 ml for 18 to 24 hours) (Wroblewski, et al. (1996) *Cancer Gene Ther.* 3: 257–264).

As can be seen from the data presented in the attached Figures, adenoviral constructs encoding β-galactosidase (β-gal) inhibited tumor cell clonogenic growth. Even with cells relatively refractory to adenovirus transduction and rAd-p53 inhibition (e.g. MDA-MB-4355; See Nielsen, et al. (1997) *Cancer Gene Ther.* 4: 129–138), a complete loss of clonogenic growth could be achieved at a PN:TC ratio of 4,250:1 in a volume of 100 ml with an 8 hour co-incubation. Furthermore, tumor cells containing wild-type p53 (e.g. MCF-7 cells) had a similar inhibition of clonogenic growth following co-incubation with either rAd-p53 or rAd-β-gal. However, the use of rAd-p53 resulted in a significantly greater inhibition of clonogenic growth of breast cancer cells expressing mutated p53 as compared to the use of rAd-β-gal.

Example 4

The Effect of PSC on rAd-p53 Induced Tumor Cell Clonogenicity

Human peripheral blood stem cells (PSC) without histological evidence of tumor cell infiltration were obtained from non-Hodgkin's lymphoma patients who were undergoing autologous PSC harvesting. PSC mononuclear cells (PMNC) were further isolated on Ficoll-Hypaque gradients (commercially available from Pharmacia LKB Biotechnology, Piscataway N.J.). 100 microliters of IMDM (Iscove's Modified Dulbecco's Medium) containing 10% fetal bovine serum (FBS), 1% glutamine and 40 micrograms/ml of gentamicin in round bottom polypropylene tubes (Becton-Dickinson) containing either $1\times10^7$ PMNC or $1\times10^7$ MDA-MB-231 cells were treated with rAd-β-gal at varying PN:cell ratios. Following incubation at 37° C., 5% $CO_2$ for 4 hours, percent inhibition of clonogenicity of tumor cells was measured in substantial accordance with the teaching of Watanabe, et al.((1996) *Blood* 87:5032–5039) using X-gal staining technology.

Figure 6:
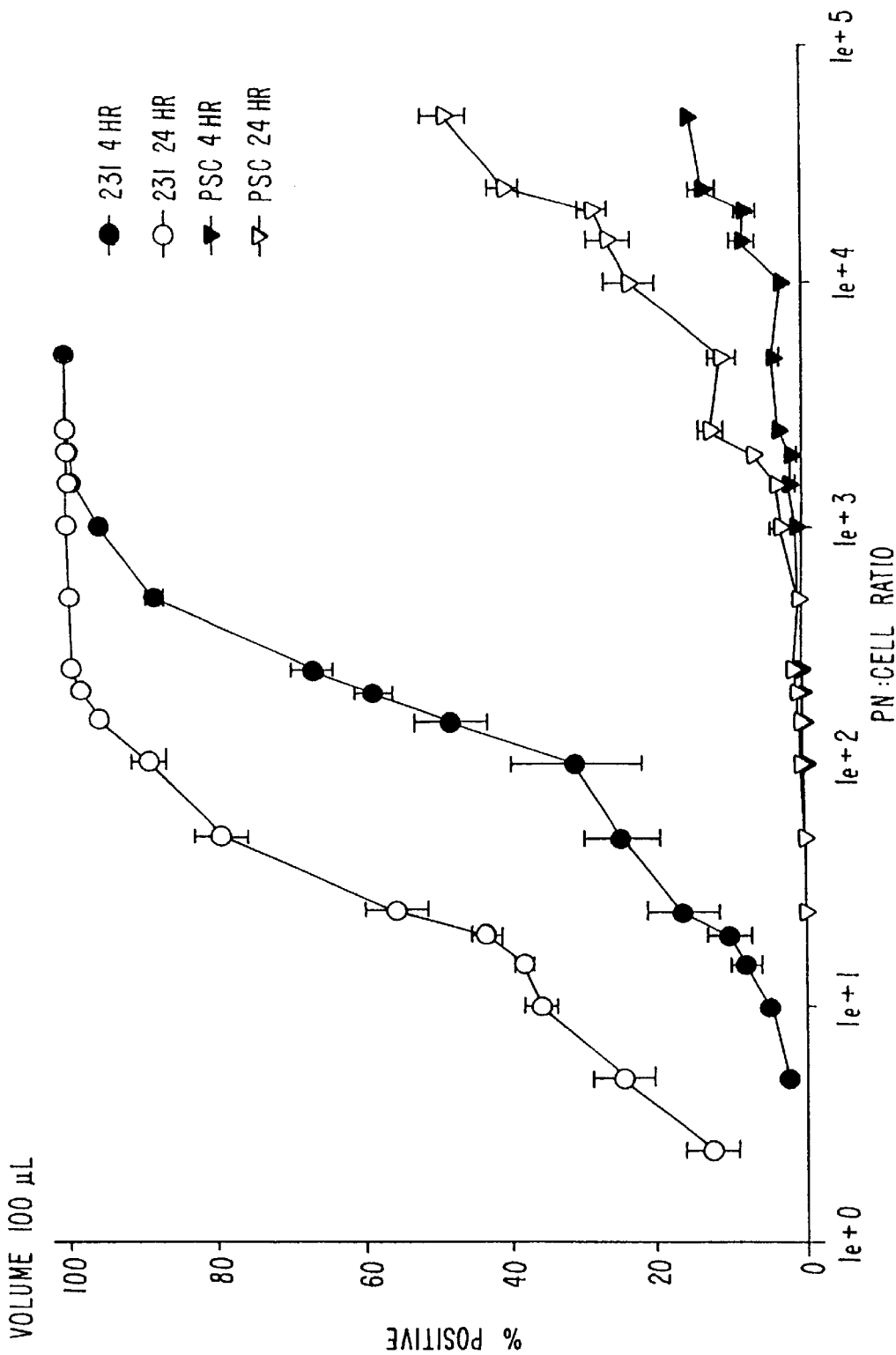
FIG. 6 is a graphical representation of the infectivity of rAd-β-gal for MDA-MB-231 cells as compared to PSC cells following either a 4 or 24 hour co-incubation at various PN:NC ratios. $1\times10^7$ MDA-MB-231 cells or PSC cells were incubated in a volume of 100 microliters for 4 or 24 hours and then stained with X-gal and the frequency of infected cells determined by cytology. Bars represent standard deviation.

As shown in FIG. 6 complete infectivity of MDA-MB-231 cells occurred at a PN:NC ratio of 400:1 following a 24 hour incubation as compared to a 40% infectivity of PSC cells at a PN:NC ratio of $5\times10^4$:1. A greater contrast in sensitivity to adenovirus infectivity was observed following a co-incubation. Thus rAd-p53 concentrations used in this purging strategy appear to be safe as they not only have no effect on the function of progenitor stem cells as measured by a granulocyte-monocyte colony forming units (CFU-GM) assay (Example 4), but also based on the low levels of infectivity of the rAd.

All publications and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

What is claimed is:

1. A method of purging tumor cells from a hematopoietic stem cell product (SCP) having from approximately $2\times10^7$ to $3\times10^8$ nucleated cells/ml (NC/ml), the method comprising the co-incubation of the stem cell product with a replication-deficient, non-integrating adenovirus (rAd) at a particle number: nucleated cell (PN:NC) ratio of approximately 2,500:1 to 250,000:1 for approximately 4 to 24 hours.

2. The method of claim 1, wherein the co-incubation time is approximately 4 to 16 hours.

3. The method of claim 1, wherein the co-incubation is performed in a total volume of about 0.1 to 2 ml.

4. The method of claim 3, wherein the co-incubation is performed in a total volume of about 0.1 to 1 ml.

5. The method of claim 1, wherein the SCP is obtained from bone marrow.

6. The method of claim 1, wherein the SCP is isolated from peripheral hematopoietic stem cells.

7. The method of claim 1, wherein the SCP is isolated from mobilized hematopoietic stem cells.

8. The method of claim 1, wherein the SCP has been enriched for CD34+ cells.

9. The method of claim 1, wherein the tumor cells are carcinoma cells.

10. The method of claim 1, wherein the tumor cells are hematopoietic tumor cells.

11. The method of claim 1, wherein the rAd comprises a DNA sequence encoding a cytotoxicity inducing factor (CIF).

12. The method of claim 11, wherein the CIF is an apoptosis inducing tumor suppressor gene.

13. The method of claim 11, wherein the CIF is a cytotoxic gene.

14. The method of claim 11, wherein the CIF is a suicide gene.

15. The method of claim 11, wherein the CIF is a toxin gene.

16. The method of claim 1, wherein the PC:NC ratio is about 25,000:1 to 250,000:1.

17. The method of claim 1, wherein the PN:NC ratio is about 2,500:1 to 25,000:1.

18. The method of claim 1, wherein the rAd is a type 5 adenovirus.

19. The method of claim 1, wherein the rAd comprises a DNA sequence encoding a cytotoxicity inducing factor (CIF).

20. The method of claim 19, wherein the CIF is an apoptosis inducing tumor suppressor gene.

21. The method of claim 19, wherein the CIF is a cytotoxic gene.

22. The method of claim 19, wherein the CIF is a suicide gene.

23. The method of claim 19, wherein the CIF is a toxin gene.

24. The method of claim 1, wherein the PC:NC ratio is about 25,000:1 to 250,000:1.

25. The method of claim 1, wherein the PN:NC ratio is about 2,500:1 to 25,000:1.

26. The method of claim 1, wherein the rAd is a recombinant adenovirus.

27. The method of claim 1, wherein the rAd is a type 5 adenovirus.

28. A method of treating an individual having a disease which is treated by myeloablative therapy and stem cell rescue using a purged product, the method comprising (a) removing a hematopoietic stem cell product from a patient in need of such treatment, (b) purging the stem cell product using a replication-deficient, non-integrating adenovirus to generate a purged product, wherein the purging comprises the co-incubation of approximately $2\times10^7$ to $3\times10^8$ nucleated cells/ml (NC/ml) from the stem cell product with a replication-deficient, non-integrating adenovirus at a PN:NC ratio of approximately 2,500:1 to 250,000:1 for approximately 4 to 24 hours, and (c) reinfusing the purged product of (b) into the patient.

29. The method of claim 28, wherein the co-incubation time is approximately 4 to 16 hours.

30. The method of claim 28, wherein the co-incubation is performed in a total volume of about 0.1 to 2 ml.

31. The method of claim 30, wherein the co-incubation is performed in a total volume of about 0.1 to 1 ml.

32. The method of claim 28, wherein the SCP is derived from bone marrow.

33. The method of claim 28, wherein the SCP is derived from peripheral stem cells.

34. The method of claim 28, wherein the SCP is derived from mobilized stem cells.

35. The method of claim 28, wherein the SCP has been enriched for CD34+ cells.

36. The method of claim 28, wherein the tumor cells are carcinoma cells.

37. The method of claim 28, wherein the tumor cells are hematopoietic tumor cells.

38. A mixture comprising approximately $2 \times 10^7$ to $3 \times 10^8$ nucleated cells/ml (NC/ml) from a hematopoietic stem cell product (SCP) and a replication-deficient, non-integrating adenovirus (rAd) at a PN:NC ratio of approximately 2,500:1 to 250,000:1.

39. The mixture of claim 38, wherein the SCP is obtained from bone marrow.

40. The mixture of claim 38, wherein the SCP is isolated from peripheral hematopoietic stem cells.

41. The mixture of claim 38, wherein the SCP is isolated from mobilized hematopoietic stem cells.

42. The mixture of claim 38, wherein the mixture comprises tumor cells.

43. The mixture of claim 38, wherein the tumor cells are carcinoma cells.

44. The mixture of claim 38, wherein the tumor cells are hematopoietic tumor cells.

45. The mixture of claim 38, wherein the rAd comprises a DNA sequence encoding a cytotoxicity inducing factor (CIF).

46. The mixture of claim 45, wherein the CIF is an apoptosis inducing tumor suppressor gene.

47. The mixture of claim 45, wherein the CIF is a cytotoxic gene.

48. The mixture of claim 45, wherein the CIF is a suicide gene.

49. The mixture of claim 45, wherein the CIF is a toxin gene.

50. The mixture of claim 38, wherein the CIF is about 25,000:1 to 250,000:1.

51. The mixture of claim 38, wherein the CIF is about 2,500:1 to 25,000:1.

52. The mixture of claim 38, wherein the rAd is a type 5 adenovirus.

* * * * *

UNITED STATES PATENT AND TRADEMARK OFFICE
CERTIFICATE OF CORRECTION

PATENT NO.    : 6,475,481 B2
DATED         : November 5, 2002
INVENTOR(S)   : James E. Talmadge It is certified that error appears in the above-identified patent and that said Letters Patent is hereby corrected as shown below:

Column 16,
Line 32, delete "PC:NC" and insert therefore -- PN:NC --;
Line 38, delete the number "1" and insert therefore -- 28 --;
Line 66, should read -- replication-deficient, non-integrating adenovirus (rAd) at a PN:NC. --

Signed and Sealed this

Thirteenth Day of July, 2004

JON W. DUDAS
*Acting Director of the United States Patent and Trademark Office*